United States Patent
Arora et al.

(10) Patent No.: US 8,367,603 B2
(45) Date of Patent: Feb. 5, 2013

(54) PROTEIN CAPABLE OF INHIBITING ANTHRAX TOXIN ACTIVITY

(75) Inventors: Naveen Arora, New Delhi (IN); Kaiser Mohammed Bijli, New Delhi (IN); Bhanu Pratap Singh, New Delhi (IN); Susheela Sridhara, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 12/839,383

(22) Filed: Jul. 19, 2010

(65) Prior Publication Data

US 2011/0014236 A1 Jan. 20, 2011

Related U.S. Application Data

(63) Continuation of application No. 10/715,482, filed on Nov. 19, 2003, now abandoned.

(51) Int. Cl.
*A01N 61/00* (2006.01)
*A61K 31/00* (2006.01)

(52) U.S. Cl. .......................... 514/1.1; 514/2.4

(58) Field of Classification Search .................. None
See application file for complete search history.

(56) References Cited

FOREIGN PATENT DOCUMENTS

WO WO-03/063768 A2 8/2003

OTHER PUBLICATIONS

Bijli et al (Abstracts from 36th Ann. Conv. of Indian College of Allergy, Asthma and Applied Immunology, Chennai (2002), Indian Journal of Allergy and Applied Immunology, Jan.-Jun. 2003, 17(1):33-44).*

Bijli, K. M., et al., "Standardizing *Imperata cylindrica*-source material for quality allergen preparations," J. Immun. Methods, vol. 260, pp. 91-96 (2002).

Bijli, K. M., et al., "Effect of various stabilizing agents on *Imperata cylindrica* grass pollen allergen extract," Clin. Exp. Allergy, vol. 33, pp. 65-71 (2003).

Zhao, P., et al., "Neutralizing monoclonal antibody against anthrax lethal factor inhibits intoxication in a mouse model," Hum. Antibodies, vol. 12, No. 4, pp. 129-135 (2003)—Abstract.

Verma, J., et al., "Purification and Partial Characterization of a 67-kD Cross-Reactive Allergen from *Imperata cylindrica* Pollen Extract," Int. Arch. Allergy Immunol., vol. 122, pp. 251-256 (2000).

Vieths, S., et al., "Current Understanding of Cross-Reactivity of Food Allergens and Pollen," Ann. N.Y. Acad. Sci., vol. 964, pp. 47-68 (2002).

Ahuja, N., et al., "Delection mutants of protective antigen that inhibit anthrax toxin both in vitro and in vivo," Biochem. Biophys. Res. Commun., vol. 307, pp. 446-450 (2003).

Bijli, K. M., et al., "An Investigation of Cross-Reactive Allergens and Antigens of *Imperata cylindrica* Using Western Blottin and ELISA Inhibition," ACI Int'l, vol. 15, No. 2, pp. 62-67 (2003).

Bijli, K. M., et al., "Single Step Purification and Characterization of a 67 kDa Major Allergen From *Imperata Cylindrica* Grass Pollen Extract," J. Allergy Clin Immunol., vol. 109, No. 1, Abstracts S133, No. 384 (2002).

Shen, S., et al., "Characterization of Proteins Responsive to Gibberellin in the Leaf-Sheath of Rice (*Oryza sativa* L.) Seedling Using Proteome Analysis," Biol. Pharm. Bull. vol. 26, No. 2, pp. 129-136 (2003).

* cited by examiner

*Primary Examiner* — Patricia A Duffy
(74) *Attorney, Agent, or Firm* — Birch, Stewart, Kolasch & Birch, LLP

(57) ABSTRACT

The invention particularly relates to inhibition of the cleavage of protective antigen (PA) of *Bacillus anthracis*, which subsequently leads to inhibition of activity of anthrax toxin.

6 Claims, 8 Drawing Sheets

(a)

(b)

(c)

(d)

(a)

(b)

Figure 1:
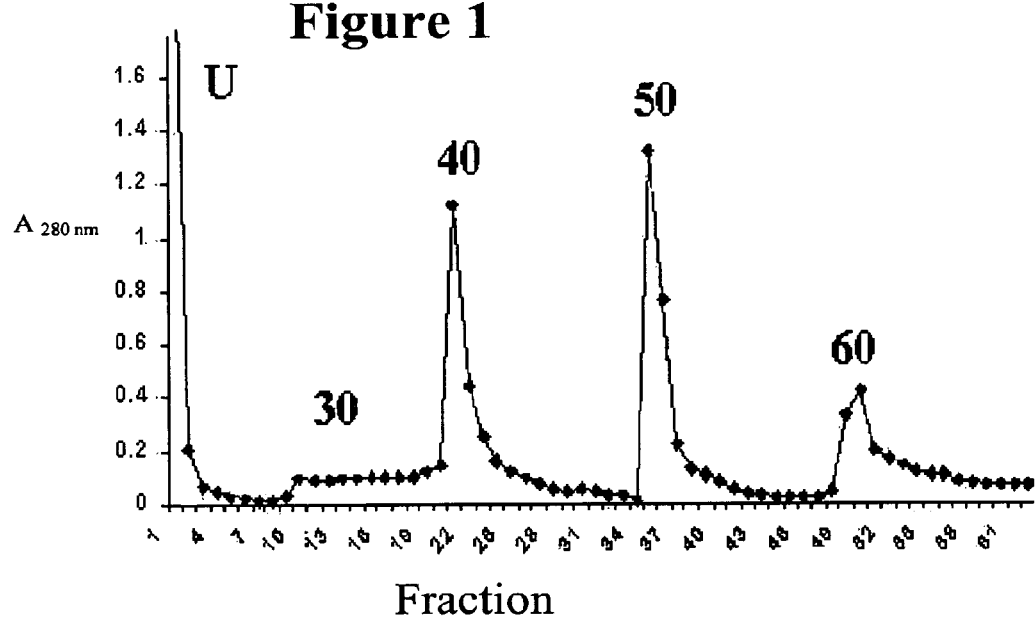
Figure 1:
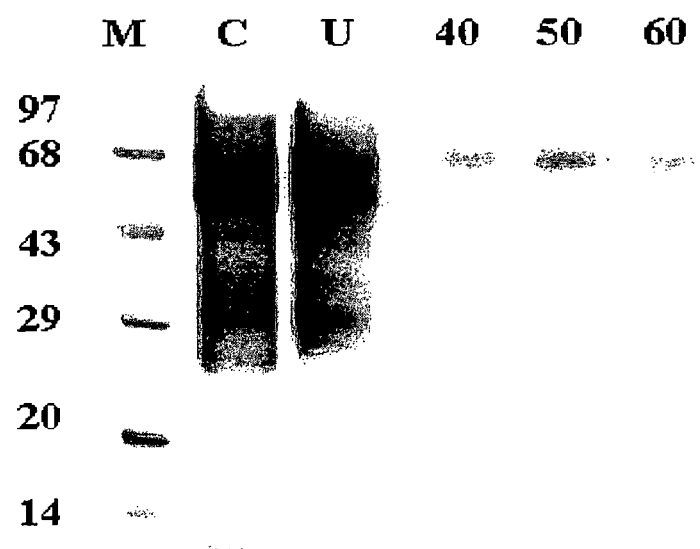
Figure 1:
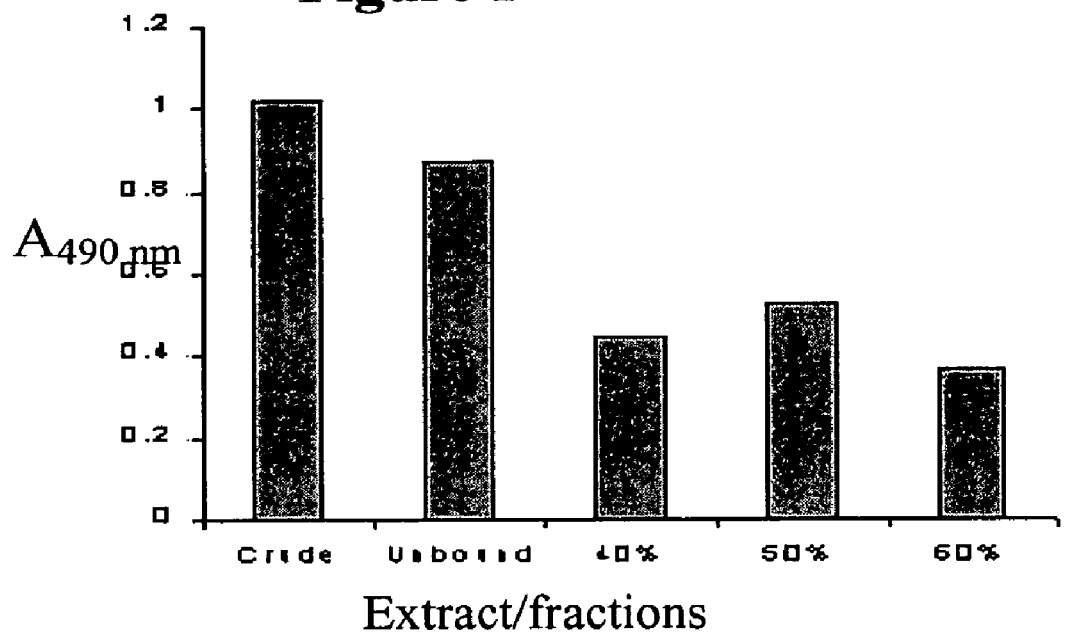
Figure 1:
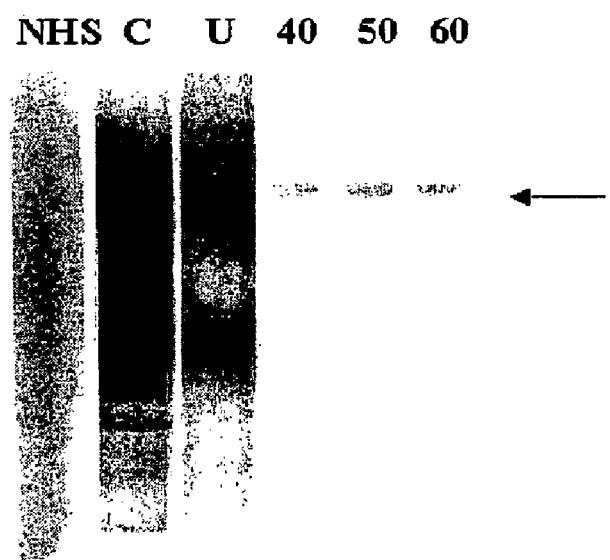

Detection of carbohydrate moieties in the purified protein

Protein/glycoprotein staining    Schiffs staining

Crude   Purified    Crude   Purified (a)

IgE Immunoblot after Periodate treatment of purified protein

1: Untreated
2: Treated 1   2

(b)

(a)

(b)

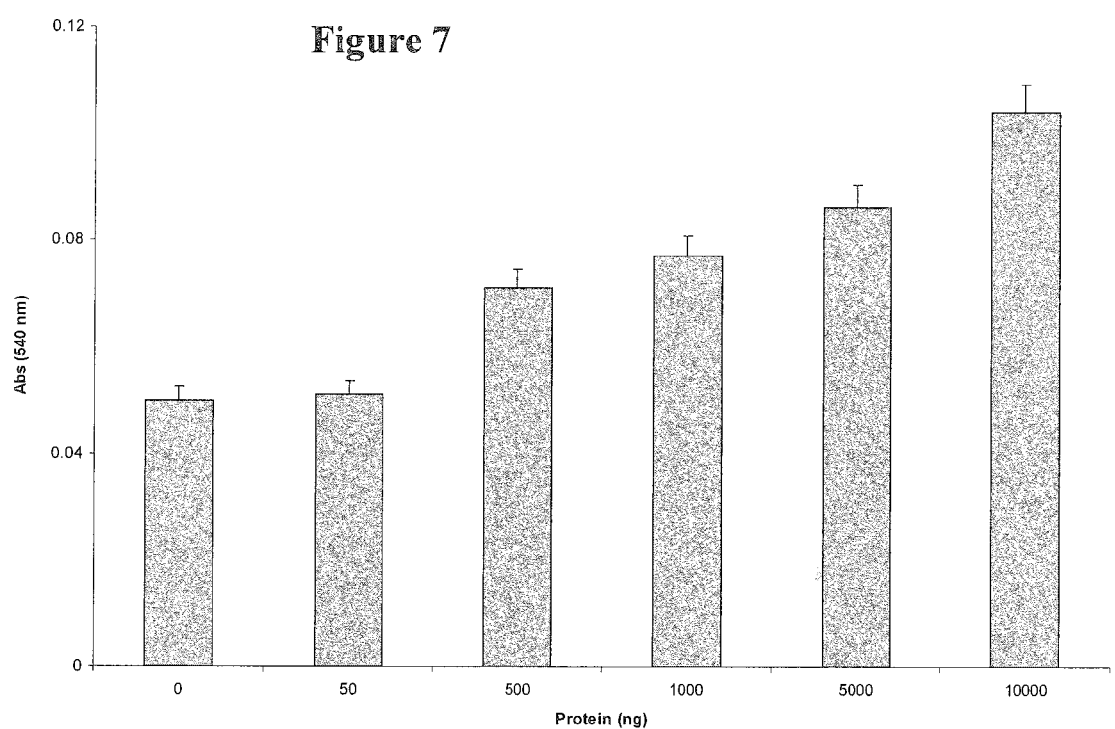

PROTEIN CAPABLE OF INHIBITING ANTHRAX TOXIN ACTIVITY

This application is a Continuation of application Ser. No. 10/715,482 filed on Nov. 19, 2003 now abandoned, and for which priority is claimed under 35 U.S.C. §120, the entire contents of which are hereby incorporated by reference.

FIELD OF INVENTION

The invention particularly relates to inhibition of the cleavage of protective antigen (PA) of *Bacillus anthracis*, which subsequently leads to inhibition of activity of anthrax toxin.

BACKGROUND OF THE INVENTION

Anthrax is a disease similar to diphtheria and tetanus and antibodies to anthrax protects against toxin and bacterial infections. PA was identified as a vaccine that would protect against *B. anthracis* infection. Further studies have shown the importance of PA as a central component for vaccine strategy. *B. anthracis* is fully virulent when it has protein toxin component and poly-D-glutamic acid capsule. The capsule plays an important role during initial stages of infection by preventing phagocytosis.

*B. anthracis* causes anthrax in animals and humans. It secretes 3 toxin components viz protective antigen (83 kDa), lethal factor and edema factor. PA is cleaved on mammalian cells by furin (in-vivo) or by trypsin (In-vitro) into 63 kDa and 20 kDa fragments. PA63 combines with lethal factor or edema factor to make lethal toxin or edema toxin, respectively. Inhibiting the PA cleavage step can abrogate anthrax toxin action. *B. anthracis* growth is inhibited by antibiotics but secretion of toxin makes it worse for the infected individual and can be lethal for the victim. The currently used vaccine for human consists of aluminium hydroxide adsorbed of a non-encapsulated strain of *B. anthracis*. Vaccine is for prevention for the onset of disease but if the person gets infected cure is not available. Antibiotics help in reducing the bacterial load but they are not effective against the toxin secreted by the bacterium. A recent report showed that a PA mutant protein inhibited anthrax toxin activity by inhibiting PA oligomerization. In present invention the inhibition of anthrax toxin activity has been shown to be inhibited a step before this, that is, by inhibiting the proteolytic cleavage of PA. Present invention therefore reports another candidate for developing a therapeutic agent that can reduce the toxic effects once the disease has set in. The invention discloses a protein molecule isolated from pollen of tropical and temperate grasses.

OBJECT OF THE INVENTION

The main object of the invention is to provide a novel protein capable of inhibiting anthrax toxin activity.

Another object of the invention is to provide a novel protein useful for prevention of PA cleavage and hence inhibiting the anthrax toxin activity.

Still another object of the invention is to provide a process for purification of the disclosed protein from pollen of grass.

Another object of the invention is to provide a novel protein for prevention of PA cleavage in-vitro and hence inhibiting the anthrax toxin activity.

One more object of the invention is to provide an improved method for purification of this protein from pollen of grass.

SUMMARY OF INVENTION

Present invention therefore relates to a novel protein for inhibition of activity of anthrax toxin. This protein has utility for developing a therapeutic agent that can reduce the toxic effects once the disease has set in. The invention discloses a protein molecule isolated from pollen of grass and a method of its purification.

The invention also discloses an improved process of protein purification from pollen extract of grass. The purified protein has the ability to inhibit protective antigen cleavage of anthrax toxin and inhibited anthrax toxin activity on mammalian cells. The protein also shows bio-activity to bind IgE antibodies.

BRIEF DESCRIPTION OF THE ACCOMPANYING FIGURES

FIG. 1

(*a*) Elution profile of the 67-kDa protein by reverse phase chromatography on octadecyl silicagel column. U: unbound fraction, 40, 50 and 60 represent the peaks obtained by elution with respective % of acetonitrile.

(*b*) SDS-PAGE (10% reducing) of crude Ic extract and eluted fractions. C: Crude Ic extract, U: unbound fraction, 40-60: fractions eluted with % acetonitrile. The protein bands were stained with CBB. M: Molecular weight marker (*c*) ELISA of Ic extract and different eluted fractions. After coating in micro-titre wells, the Ic extract, unbound fraction, purified fraction was incubated with Ic hypersensitive-pooled patient's sera ($1/10$ v/v). The bound IgE was determined using anti-human IgE-HRP ($1/1000$ v/v). The color was developed using OPD. The values represent $A_{490\ nm}$.

(*d*) IgE immunoblot of crude (C), unbound (U) and purified fractions. The proteins were transferred onto nitrocellulose and incubated with Ic hypersensitive pooled patient's sera ($1/10$ v/v). Normal Human Sera (NHS) was used as control. The bound IgE was probed with anti-human IgE-HRP ($1/1000$ v/v). The color was developed using DAB.

Figure 2:
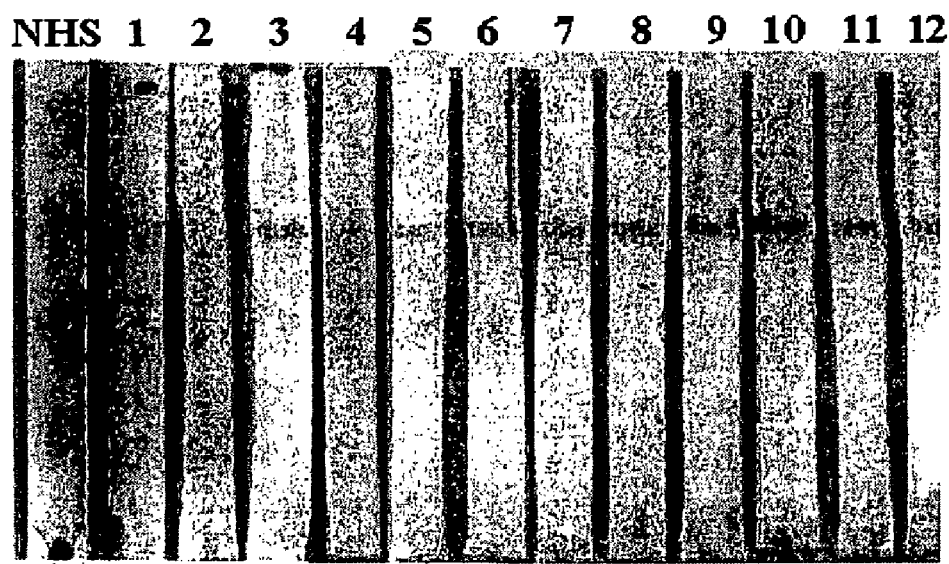

FIG. 2 IgE immunoblot of the purified protein using individual patient's sera. The protein after electrophoresis was transferred to nitrocellulose. Strips were cut and incubated separately with 12 Ic hypersensitive individual patient's sera ($1/10$ v/v). Normal Human Sera (NHS) was used as control. The bound IgE was probed using anti-human IgE-HRP ($1/1000$ v/v). The color was developed using DAB.

Figure 3:
Figure 3:
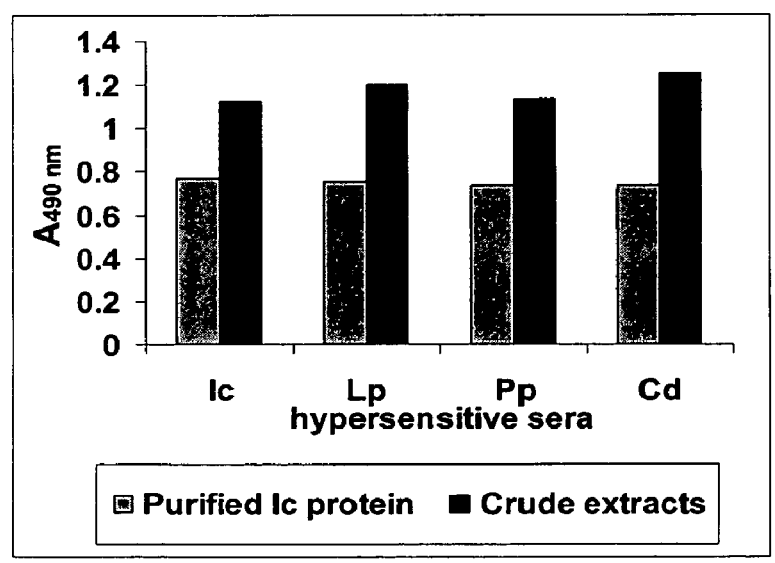

FIG. 3(*a*) Immunoblot of the purified 67-kDa protein with hypersensitive sera to Ic: *Imperata cylindrica;* Lp: *Lolium perenne;* Pp: *Phleum pratense* and Cd: *Cynodon dactylon*. The electrophoresed proteins were transferred to nitrocellulose and incubated with respective sera ($1/10$ v/v). The bound IgE was probed using anti-human IgE-HRP ($1/1000$ v/v). The color was developed using DAB. (*b*) ELISA of the purified 67-kDa protein with different hypersensitive sera as mentioned in (*a*). The protein was coated (1 µg/well) in microtitre well and incubated with different hypersensitive sera ($1/10$ v/v). The bound IgE was determined using anti-human IgE-HRP antibody ($1/1000$ v/v). The color was developed using OPD and values represent $A_{490\ nm}$.

Figure 4:
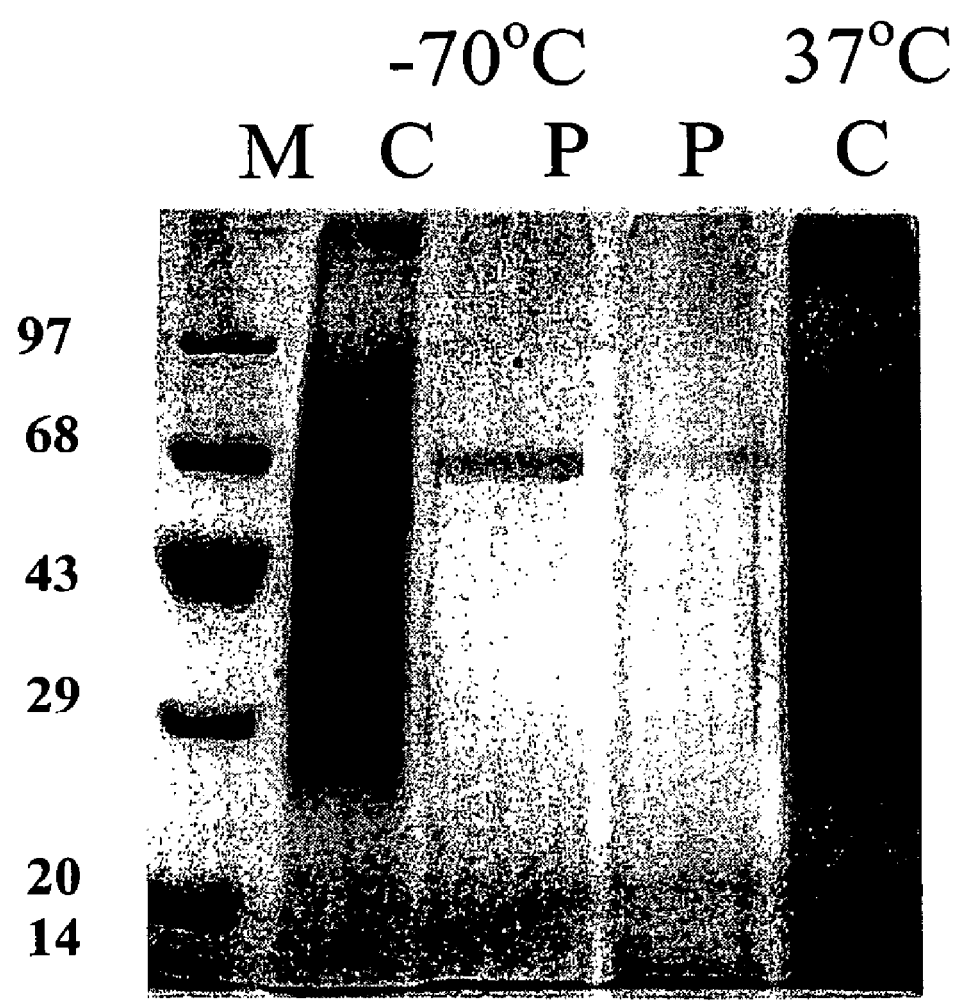

FIG. 4 SDS-PAGE of the 67-kDa protein purified from extracts prepared from freeze-dried (−70° C.) and oven-dried (37° C.) Ic pollen, M: Molecular weight marker, C: Crude Ic extract, P: Purified protein.

Figure 5:
Figure 5:

FIG. 5(*a*) Digoxigenin and fluorescein labeling of glycoproteins (panel 1) Schiff's staining for detection of carbohydrate (panel 2). (*b*) Periodate treated purified protein.

Figure 6:
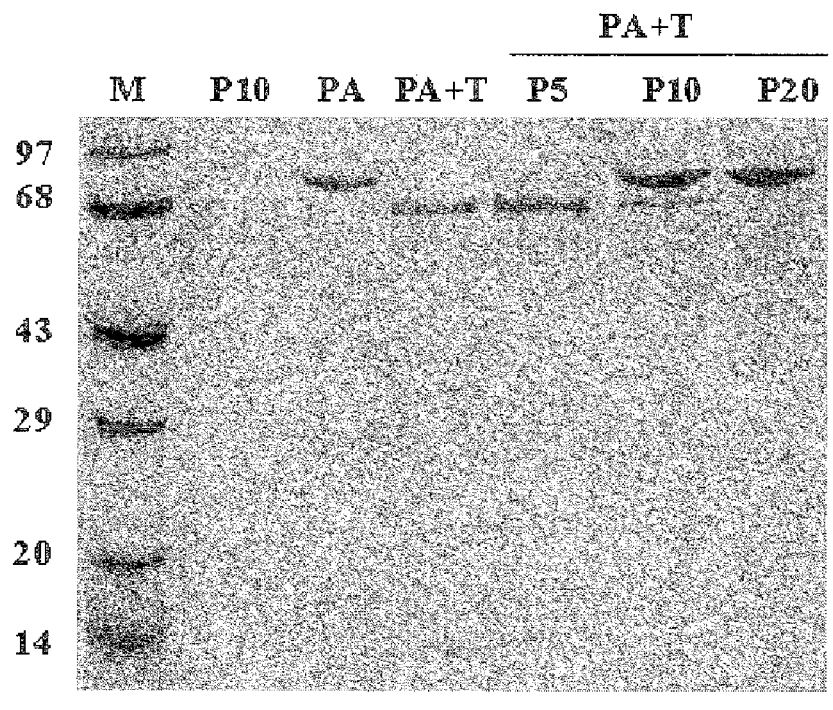
Figure 6:
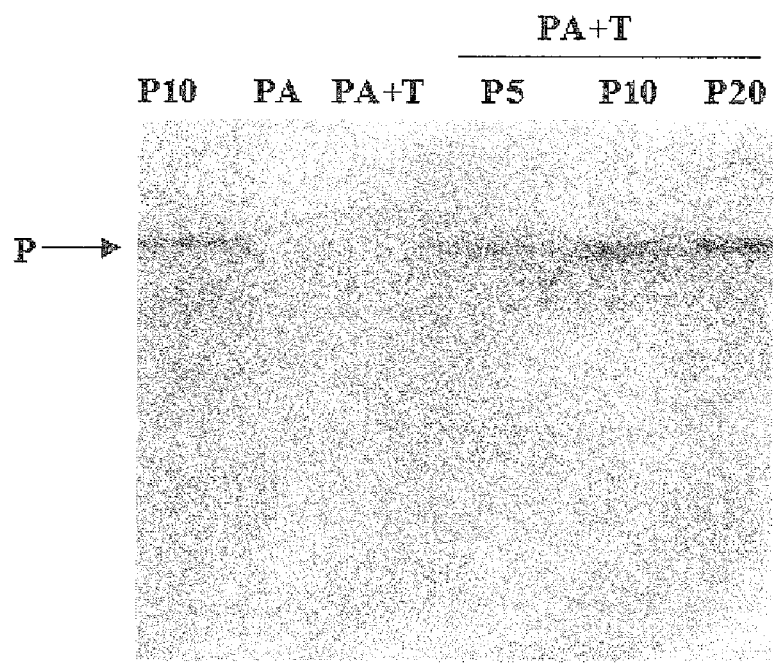

FIG. 6 SDS-PAGE (*a*) and Immunoblot using Ic hypersensitive sera (*b*) of inhibition of protective antigen (PA) cleavage with trypsin (T). P10: 10 ng of purified 67-kDa protein, PA: 5 µg of protective antigen, PA+T: 5 µg of PA with 25 ng of T, P5-P20: PA with T in presence of 5, 10 and 20 ng of purified 67-kDa protein. The bands were observed after CBB staining. M: Molecular weight marker.

FIG. 7 Inhibition of anthrax toxin activity on J774A.1 cells: Cells were treated with PA and LF (500 ng each) and 50-10000 ng of purified 67-kDa protein was added. Cells were incubated for 3 hr and viability was determined by MTT assay.

DETAILED DESCRIPTION OF THE INVENTION

Present invention relates to a novel protein for inhibition of activity of anthrax toxin. This protein has utility for developing a therapeutic agent that can reduce the toxic effects once the disease has set in. The invention discloses a protein molecule isolated from pollen of grass and a method of its purification.

The pollen collected from inflorescence of grass such as *I. cylindrica* was extracted in appropriate buffer followed by protein purification, The purified protein of interest was checked for its purity and for the proteolytic activity, if any, on 3 different substrates. The protein was also checked for its stability. It was assayed for biological activity, that is, inhibition of cleavage of protective antigen (PA) of anthrax toxin.

Preparation of pollen extract; *Imperata cylindrica* (Ic) inflorescence was collected during peak pollen season in and around Delhi Metropolis. The pollens were sieved and its purity was determined. The pollen was extracted in phosphate buffered with physiological saline pH 7.4 or Ammonium bicarbonate buffer. The pollen extract was dialyzed, lyophilized and protein was estimated by Lowry's method.

Protein purification: The extracted protein was loaded on the pre-equilibrated octadecyl silica gel or like material. The eluted protein was further loaded on the similar pre-equilibrated column to improve binding of the protein of interest with the gel matrix. The unbound material in the column was washed with distilled water till the absorbance with 280 became zero. The bound material was eluted with step acetonitrile gradient containing water and fluoroacetic acid. The fractions obtained were freeze-dried. The purity of the protein was determined by SDS-PAGE and Western blot and protein was estimated by Lowry's method. The protein showed a single band in SDS-PAGE and Western blot.

Proteolytic activity of the purified protein; The proteolytic activity of the purified protein was determined on substrates such as gelatin, bovine serum albumin and casein hydrolysate. The purified protein showed no activity on these substrates.

Stability of the purified protein: The purified protein was checked for its stability at 37° C. The protein was kept at 37° C. and 4° C. overnight (16 h) in the solution form. ELISA and the Western blot of the treated purified protein showed no difference in activity (FIG. 4).

Glycoprotein staining: Purified 67-kDa protein revealed absence of carbohydrate moities. These were confirmed through Skiff's staining and periodate oxidation. (FIG. 5)

PA cleaving activity of the purified protein: The biological activity of the purified protein was determined on protective antigen cleavage. Protective antigen was cleaved with trypsin in presence and absence of the purified protein in a dose dependent manner at room temperature. PA without any inhibitor (purified protein) was observed to be completely cleaved with trypsin. In presence of inhibitor (purified protein), at lower concentration (5 ng), the PA was also completely cleaved while at a little higher concentration (10 ng) the protein blocked some cleavage activity of PA. At still higher concentration (20 ng) the protective antigen cleavage was completely inhibited, This complete inhibition of activity will abrogate the toxin action completely. (FIG. 6)

Inhibition of anthrax toxin activity with 67-kDa protein: An assay was performed to determine the inhibition of anthrax toxin activity on J1774A.1 macrophage cell line using graded amounts of the purified 67-kDa protein with 500 ng each of PA and lethal factor. Briefly, the cells were grown overnight to 80% confluence in DMEM containing 10% fetal bovine serum and 2 mM glutamine in a cell culture plates. The cells were preincubated with 50 ng to 10,000 ng of purified 67-kDa protein for 1 hour with media and further incubated with 500 ng each of PA and lethal factor (LF) for 3 hours. The cell viability was determined by incubating 3-[4,5-domethylthiazol-2-yl]-2,5-diphenyltetrazolium bromide (MTT) for 2 hr. Cells incubated without 67-kDa protein were used as control. The cells were dissolved in 90% proponal with 0.5% SDS. The absorbance was read at 540-nm using microplate reader (FIG. 7).

Characterization of the Purified Protein:

IgE binding: ELISA with purified protein fractions using Ic hypersensitive-pooled sera demonstrated IgE binding in the range of 0.365-0.525 ($A_{490}$ nm) with the highest absorbance in 50% acetonitrile (FIG. 1c). All the three fractions having 67-kDa protein were pooled and immunoblotted with twelve Ic hypersensitive individual patient's sera. IgE binding was observed with 10 out of the 12 sera demonstrating it to be a major allergen (FIG. 2).

Cross-reactivity: FIG. 3a shows the cross-reactivity of 67 kDa hypersensitive sera specific to *Imperata cylindrica, Cynodon dactylon, Lolium perenne* and *Phleum pratense*. ELISA with these sera showed close similarity between the OD values obtained for 67-kDa protein and crude extracts of these grasses (FIG. 3).

Stability: This purified 67-kDa protein was isolated from pollen grains processed at 37° C. (FIG. 4, lane 4). This shows that the 67-kDa protein is stable and does not degrade during processing at harsh conditions. To further test the stability of the 67-kDa purified protein, it was kept at 37° C. or 4° C. overnight and assessed by ELISA and Immunoblot using Ic-hypersensitive pooled patient's sera. No difference was recorded in IgE binding of the protein kept at two temperatures (4° C. $A_{490\,nm}$ 0.767 & 37° C. $A_{490\,nm}$ 0.755). Immunobloting demonstrated similar activity in both the samples of 4° C. and 37° C. incubated 67-kDa protein suggesting it to be a thermostable protein.

Carbohydrate determination: The experiments for carbohydrate detection revealed that the 67-kDa protein was devoid of carbohydrate moiety. Further it did not show any difference in IgE binding after periodate treatment (FIG. 5).

Proteolytic activity: The protein did not show any proteolytic activity on BSA, gelatin and casein hydrolysate. However, crude Ic extract demonstrated proteolytic activity (Data not shown). The 67-kDa protein was treated with trypsin to get the sequence of cleaved peptides. But trypsin treatment did not show any degradation of the purified protein on SDS-PAGE and immunoblot (Data not shown).

Inhibition of proteolytic activity: PA was cleaved completely by trypsin into 63 kDa and 20 kDa fragments as seen by SDS-PAGE (FIG. 6a lane 4). PA with trypsin containing 5 ng of 67-kDa protein showed complete cleavage (FIG. 6a lane 5), 10 ng of the protein showed partial cleavage (FIG. 6a lane 6) and 20 ng of protein showed complete inhibitory activity (FIG. 6a lane 7). Immunoblot showed that the 67-kDa protein remained intact even after trypsin digestion (FIG. 6b lane 1, 4, 5 and 6). It shows that trypsin has no action on 67-kDa protein.

Inhibition of anthrax toxin activity in eukaryotic cells: Inhibition of anthrax toxin activity was determined on macrophage cell line sensitive to anthrax toxin lethal factor. J774A.1 cells were incubated with 67-kDa protein in presence of 500 ng each of PA and LF showed inhibition of anthrax toxin activity (FIG. 7). Cells incubated with PA and LF were destroyed by the action of anthrax toxin. The 67-kDa protein showed dose dependent inhibition of anthrax toxin activity (FIG. 7). Cells containing 67-kDa protein were protected and thereby an increase in cell viability was evident.

Accordingly, the main embodiment of the present invention relates to a novel protein capable of inhibiting anthrax toxin activity said protein comprising of following characteristics:
(i) Hydrophobic in nature,
(ii) Molecular weight 67 kDa,
(iii) Stable at room temperature,
(iv) Resistant to trypsin,
(v) Having no proteolytic activity,
(vi) Inhibits proteolytic cleavage of protective antigen (PA) of *B. anthracis* in a dose dependent manner,
(vii) Binds to IgE, and
(viii) The protein is devoid of any carbohydrate moiety.

Another embodiment of the present invention relates to the protein wherein the said protein is isolated from the pollen grains of grass species selected from group of *Imperata cylindrica* (Ic), *Lolium perenne, Phleum pratense, Cynodon dactylon* and related genus.

Still another embodiment of the present invention relates to the protein wherein the said protein is stable in the temperature range of about 3° C. to 40° C.

In another embodiment of the present invention the said the protein is stable in the temperature range of about 4° C. to 37° C.

Yet another embodiment of the present invention relates to the wherein protein in the range of about 25-20 ng completely inhibits the protective antigen (PA) of the anthrax toxin.

One more embodiment of the present invention relates to the protein wherein the protein in the range of about 15-5 ng partially blocks the cleavage activity of the PA.

Still another embodiment of the present invention relates to the protein wherein the protein in the range of about 25 ng to 11,000 ng is efficient in inhibiting the anthrax toxin activity.

Another embodiment of the present invention relates to protein wherein the protein in the range of about 50 ng to 10,000 ng is efficient in inhibiting the anthrax toxin activity.

In yet another embodiment of the present invention relates to a process of purification of the novel protein capable of inhibiting anthrax toxin activity, said process comprising steps of:
a. extracting the total protein from the grass pollen by suspending the pollen in phosphate buffer for a period of about 3 h to 15 h under stirring continuously under cold conditions followed by high speed centrifugation at 15,000 rpm,
b. purifying protein fractions from the extract of step (a) by column chromatography,
c. lyophilizing the dialyzed protein fraction containing the protein of interest obtained in step (b),
d. subjecting the protein fractions of step (iii) to SDS-PAGE followed by Western blotting and immuno-staining to separate and locate the protein of interest,
e. testing the ability of the purified protein to inhibit anthrax toxin activity by incubating the isolated protective antigen (PA) of *B. anthracis* with or without lyophilized isolated protein from a grass in presence of trypsin for measuring the PA cleaving (inhibitory) activity of the isolated protein by SDS-PAGE in a dose dependent manner, and
f. characterizing the purified protein allergenic activity by SDS-PAGE, Western blotting and immuno-staining.

Another embodiment of the present invention relates to the pollen grains wherein the pollen grains for purification of the protein in the step (a) are collected from grasses selected from group comprising of *Imperata cylindrica* (Ic), *Lolium perenne, Phleum pratense, Cynodon dactylon* and related genus.

Yet another embodiment of the present invention relates to the buffer used for extraction of pollen in the step (a) is selected from group comprising of 0.1M PBS or 0.1 M ammonium bicarbonate of pH ranging from 7.0 to 8.0.

Still another embodiment of the present invention relates to the material used for the column chromatography in step (b) is a hydrophobic resin selected from octadecyl silica gel and similar silica gels.

One more embodiment of the present invention relates to the protein bound to the chromatography column in step (c) is eluted with acetonitrile in range of about 30-75% and about 0.50% Trifluoroacetic acid (TFA) in water.

Another embodiment of the present invention relates wherein the acetonitrile is in the range of about 40-60% and TFA is about 0.1% in water.

One more embodiment of the present invention relates to the protein wherein the protein in the range of about 25-20 ng completely inhibits the protective antigen (PA) of the anthrax toxin.

Still another embodiment of the present invention relates to the protein wherein the protein in the range of about 15-5 ng partially blocks the cleavage activity of the PA.

Yet another embodiment of the present invention relates to the protein wherein the protein in the range of about 25 ng to 11,000 ng is efficient in inhibiting the anthrax toxin activity.

Another embodiment of the present invention relates to the protein wherein the protein in the range of about 50 ng to 10,000 ng is efficient in inhibiting the anthrax toxin activity.

The following examples concerning the novel protein capable of inhibiting anthrax toxin activity are provided to illustrate the invention and should not be construed to limit the scope of the invention.

EXAMPLES

Example 1

Reagents: The reagents used were from standard manufacturing agent. Octadecyl Silica gel is purchased from Sigma and PA was a gift from Dr. Yogendra Singh (IGIB, mall road Delhi 110007).

Example 2

Protein extraction: The inflorescence of a tropical grass such as *Imperata cylindrica* (Ic) was collected during the peak flowering season (April-May) and frozen instantly at minus 70° C. The pollens were sieved after lyophilizing the material. The pollens were defatted with diethyl ether with 3 changes. Extraction was done by adding 1 g of pollen in 50 ml of phosphate buffer saline (0.1M, saline 0.9%) pH 7.2. It was stirred for 4 hr on a magnetic stirrer and then centrifuges at 15,000 rpm for 30 min at 4° C. The supernatant obtained was termed as Ic extract.

Example 3

Protein extraction: The inflorescence of a tropical grass such as *Imperata cylindrica* (Ic) was collected during the peak flowering season (April-May) and frozen instantly at minus 70° C. The pollens were sieved after lyophilizing the material. The pollens were defatted with diethyl ether with 3 changes. Extraction was done by adding 1 g of pollen in 50 ml of 50 mM ammonium bi carbonate buffer pH 7.4. It was stirred for 4 hr on a magnetic stirrer and then centrifuges at 15,000 rpm for 30 min at 4° C. The supernatant obtained was termed as Ic extract.

Example 4

Protein Purification: Octadecyl silica gel (0.5 grams) [Sigma USA] was packed into 1 ml column in 100% acetonitrile. The column was washed with 50 ml acetonitrile and equilibrated with 20 ml distilled water. Ten milligrams of the lyophilized Ic extract was loaded on the column and unbound fraction was recycled 5 times to ensure maximum binding. The column was washed with distilled water till the $A_{280\ nm}$ became zero. The bound proteins were eluted with 15 ml each of 40, 50 and 60% acetonitrile in water containing 0.1% trifluoroacetic acid. The fractions were freeze dried and stored at −20° C. until further analysis for bio-activity. (FIG. 1)

Example 5

SDS-PAGE and Immunobloting: SDS-PAGE (10% separation gel) vertical slab gel and immunoblot of extract and purified protein (4 ug and 2 ug respectively) was carried out as per method given in "Short protocols in Molecular Biology, 1995". The Protein bands were stained with Commassie brilliant blue R and destained as per Short protocols in Molecular biology (1995). The electrophoresed proteins/fractions were transferred to nitrocellulose (150 m amp for 4 hr), non-specific sites blocked with 3% defatted milk and incubated with Ic-hypersensitive pooled patient's sera (1/10, v/v) overnight at 4° C., The bound IgE was probed by incubating with anti-human IgE-HRP (1/000 v/v, Sigma USA) and color development using diaminobenzidine. (FIG. 3 and FIG. 4)

Example 6

Demonstration of bio-activity of purified protein inhibiting PA cleaving: For its activation protective antigen (PA) is cleaved by a protease. On activation, it binds to lethal factor or edema factor of anthrax toxin to be delivered to the cell. Inhibition of protective antigen cleavage blocks the anthrax toxin action. The protease inhibitory activity of 67-kDa protein was determined on anthrax toxin protective antigen (PA). PA (83 kDa) on cleavage with trypsin in solution gives a 63 kDa and 20 kDa protein. To determine the trypsin inhibitory activity 5 µg PA (a gift from Dr. Y Singh) was incubated with 20 ng of trypsin in HEPES buffer (10 mM pH 7.0) containing 1 mM $CaCl_2$ for 30 min at 37° C. either alone or with 5, 10 and 20 ng of purified 67-kDa protein. The reaction was stopped by addition of 2× sample buffer (0.5 ml of 1.25M Tris pH6.8 with 0.8 g of SDS and 0.5 ml of beta mercaptoethanol and 1 mg bromo phenol and made the volume with 10 ml) and run for SDS-PAGE and Western blot. (FIG. 6)

Example 7

Inhibition of anthrax toxin activity with 67-kDa protein: An assay was performed to determine the inhibition of anthrax toxin activity on J774A.1 macrophage cell line using graded amounts of the purified 67-kDa protein with 500 ng each of PA and lethal factor. Briefly, the cells were grown overnight to 80% confluence in DMEM containing 10% fetal bovine serum and 2 mM glutamine in a cell culture plates. The cells were preincubated with 50 ng to 10,000 ng of purified 67-kDa protein for 1 hour with media and further incubated with 500 ng each of PA and lethal factor (LF) for 3 hours. The cell viability was determined by incubating 3-[4,5-domethylthiazol-2-yl]-2,5-diphenyltetrazolium bromide (MTT) for 2 hr. Cells incubated without 67-kDa protein were used as control. The cells were dissolved in 90% proponal with 0.5% SDS. The absorbance was read at 540-nm using plate reader (FIG. 7)

Advantages of the Invention

The currently used vaccine against anthrax consists of aluminum hydroxide adsorbed on a non-encapsulated strain of *B. anthracis*. Vaccine is for prevention for the onset of disease but if the person gets infected cure is not available. Antibiotics help in reducing the bacterial load but they are not effective against the toxin secreted by the bacterium. The purified protein works independent to the antibiotic and inhibits the cleavage of the protective antigen. The inhibition of protective antigen cleavage abrogates the anthrax toxin activity. The protein disclosed in the invention inhibits protective antigen cleavage, thereby inhibiting the anthrax toxin activity. Therefore, in the present invention a candidate molecule is disclosed which is useful for developing a therapeutic agent that can reduce the toxic effects once the disease has set in.

We claim:

1. A method for inhibiting anthrax toxin activity comprising contacting said anthrax toxin with a protein having the following characteristics:
    (i) hydrophobic in nature,
    (ii) molecular weight 67 kDa,
    (iii) stable at room temperature,
    (iv) resistant to trypsin,
    (v) has no proteolytic activity,
    (vi) inhibits proteolytic cleavage of protective antigen (PA) of *Bacillus anthracis* in a dose dependent manner,
    (vii) binds to IgE, and
    (viii) devoid of any carbohydrate moiety; and
    (ix) obtained from pollen grains of a grass *Imperata cylindrica*.

2. The method of claim 1 wherein said protein is stable in the temperature range of about 3° C. to 40° C.

3. The method of claim 1 wherein said protein is stable in the temperature range of about 4° C. to 37° C.

4. The method of claim 1, wherein an amount of the protein in the range of about 25-20 ng completely inhibits the cleavage of 5 µg of the protective antigen of *Bacillus anthracis* by trypsin.

5. The method of claim 1, wherein an amount of the protein in the range of about 15-5 ng partially inhibits the cleavage of 5 µg of the protective antigen of *Bacillus anthracis* by trypsin.

6. The method of claim 1 wherein the protein is isolated using hydrophobic column chromatography.

* * * * *